(12) United States Patent
Dukan et al.

(10) Patent No.: US 11,187,705 B2
(45) Date of Patent: Nov. 30, 2021

(54) METHOD FOR LABELING SPECIFICALLY LIVING MICROORGANISMS COMPRISING THE USE OF MODIFIED MONOSACCHARIDE COMPOUNDS

(71) Applicants: CENTRE NATIONAL DE LA RECHERCHE SCIENTIFIQUE (CNRS), Paris (FR); UNIVERSITE D'AIX-MARSEILLE, Marseilles (FR); UNIVERSITE PARIS SUD, Orsay (FR)

(72) Inventors: Sam Dukan, Marseilles (FR); Boris Vauzeilles, Sceaux (FR); Jordi Mas Pons, Rubi (ES); Aurélie Baron, L'isle Adam (FR)

(73) Assignees: CENTRE NATIONAL DE LA RECHERCHE SCIENTIFIQUE (CNRS), Paris (FR); UNIVERSITE D'AIX-MARSEILLE, Marseilles (FR); UNIVERSITE PARIS-SACLAY, Gif-Sur-Yvette (FR)

( * ) Notice: Subject to any disclaimer, the term of this patent is extended or adjusted under 35 U.S.C. 154(b) by 460 days.

(21) Appl. No.: 15/570,410

(22) PCT Filed: May 3, 2016

(86) PCT No.: PCT/EP2016/059864
§ 371 (c)(1),
(2) Date: Oct. 30, 2017

(87) PCT Pub. No.: WO2016/177712
PCT Pub. Date: Nov. 10, 2016

(65) Prior Publication Data
US 2018/0143200 A1    May 24, 2018

(30) Foreign Application Priority Data
May 4, 2015    (EP) ..................................... 15166249

(51) Int. Cl.
*G01N 33/58* (2006.01)
*C12Q 1/04* (2006.01)
(Continued)

(52) U.S. Cl.
CPC ............. *G01N 33/582* (2013.01); *C12Q 1/02* (2013.01); *C12Q 1/04* (2013.01);
(Continued)

(58) Field of Classification Search
None
See application file for complete search history.

(56) References Cited

U.S. PATENT DOCUMENTS 9,057,093 B2 * 6/2015 Fovet ....................... C12Q 1/04
9,181,204 B2 * 11/2015 Leibl .................... C07D 249/06
(Continued)

FOREIGN PATENT DOCUMENTS

EP    2 617 833    7/2013
EP    3091082 A1 * 11/2016 ............... C12Q 1/02
(Continued)

OTHER PUBLICATIONS

Dumont et al, Laboratoire de Chimie, Institutde Microniologie de la Mediterranee (IMM) Bacteeeerienne (UMR 7283), Aix Marrrrseille Universite, Marsielle, 13402, Fr. Angewandte Chimie, International Edition, 2012 (Abstract Only) (Year: 2012).*
Mas Pom et al, Abstracts of Papers, 248th ACS National Meeting & Exposition, San Francisco, CA, United States, Aug. 10-14, 2014 (2014), CARB-97. American Chemical Society: Washington, D. C. (Abstract Only) (Year: 2014).*
(Continued)

*Primary Examiner* — Nita M. Minnifield
(74) *Attorney, Agent, or Firm* — Nixon & Vanderhye, P.C.

(57) ABSTRACT

The invention relates to a method for labeling specifically living microorganisms in a sample comprising microorganisms, the method comprising the steps of: a) incubating said microorganisms of said sample with at least one modified monosaccharide compound comprising a first reactive chemical group capable to chemically react with a second reactive group, so that a residue bearing said first reactive group is incorporated into such microorganisms, and b) contacting said residue incorporated in the microorganisms, with a labeling molecule comprising a said second reactive group, for generating the chemical reaction of said first reactive group of said residue incorporated within said living microorganisms with said second reactive group of said labeling molecule, resulting in a covalent link, characterized in that the said modified monosaccharide compound has the following formula (I'), or a salt thereof: —X can be O, NH or S, preferably O and NH, and —R1 and R2 can be independently H, OH, $NH_2$, OH and $NH_2$ being substituted or not by protecting groups thereof, preferably substituted by alkyl, hydroxyalkyl, acyl, formyl or imidoyl groups, and —R3 is H or an alkyl chain in $C_1$ to $C_4$, each carbon being substituted or not substituted by OH or $NH_2$ substituted or not by protecting groups thereof, preferably by alkyl, hydroxyalkyl, acyl, formyl or imidoyl groups, and —at least one of X, R1, R2 and R3 groups, preferably R3, being substituted by a said first reactive group Ra.

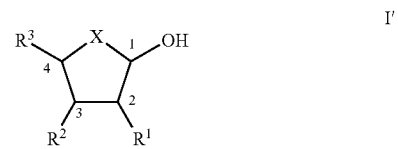

13 Claims, No Drawings

(51) Int. Cl.
  *G01N 33/569* (2006.01)
  *C12Q 1/02* (2006.01)
(52) U.S. Cl.
  CPC .. *G01N 33/56905* (2013.01); *G01N 33/56911*
    (2013.01); *G01N 33/56916* (2013.01); *G01N*
    *33/56938* (2013.01); *G01N 33/56961*
    (2013.01); *Y02A 50/30* (2018.01)

(56) References Cited

U.S. PATENT DOCUMENTS

| | | | | |
|---|---|---|---|---|
| 9,181,575 | B2* | 11/2015 | Fovet | C12Q 1/06 |
| 9,492,473 | B2* | 11/2016 | von Maltzahn | A61K 31/715 |
| 9,493,809 | B2* | 11/2016 | Dukan | C12Q 1/04 |
| 10,082,509 | B2* | 9/2018 | Dukan | G01N 33/56911 |
| 10,571,469 | B2* | 2/2020 | Dukan | C12Q 1/04 |
| 2008/0268468 | A1 | 10/2008 | Wong et al. | |
| 2014/0363817 | A1* | 12/2014 | Dukan | C12Q 1/04 |
| | | | | 435/6.11 |
| 2016/0238609 | A1* | 8/2016 | Dukan | C12Q 1/02 |
| 2016/0289730 | A1* | 10/2016 | Pezacki | C12Q 1/04 |
| 2017/0030908 | A1* | 2/2017 | Dukan | C12Q 1/04 |
| 2018/0143193 | A1* | 5/2018 | Dukan | C12Q 1/02 |
| 2018/0143200 | A1* | 5/2018 | Dukan | C12Q 1/02 |
| 2020/0158727 | A1* | 5/2020 | Dukan | G01N 33/56911 |

FOREIGN PATENT DOCUMENTS

| | | | | |
|---|---|---|---|---|
| WO | WO 2013/107759 | | 7/2013 | |
| WO | WO-2013107759 | A1 * | 7/2013 | |
| WO | WO-2015063173 | A1 * | 5/2015 | |
| WO | WO-2015074141 | A1 * | 5/2015 | |
| WO | WO-2016177724 | A1 * | 11/2016 | C12Q 1/02 |

OTHER PUBLICATIONS

Jaipuri et al (Synthesis and Quantitative Evaluation of Glycero-D-manno-heptose Binding to Concanavalin A by Fluorous-Tag Assistance, Angew. Chem. Int. Ed., vol. 47, No. 9, Jan. 18, 2008 (Jan. 18, 2008), pp. 1707-1710) (Year: 2008).*
Sadamoto et al (Bacterial Surface Engineering Utilizing Glucosamine Phosphate Derivatives as Cell Wall Precursor Surrogates, Chemistry—A European Journal, vol. 14, No. 33, Nov. 17, 2008 (Nov. 17, 2008), pp. 10192-10195) (Year: 2008).*
International Search Report and Written Opinion of the ISA for PCT/EP2016/059864 dated Jun. 23, 2016, 12 pages.
Chung et al., "Dioxygenases in Burkholderia ambifaria and Yersinia pestis that hydroxylate the outer Kdo unit of lipopolysaccharide", Proceedings of the National Academy of Sciences, vol. 108, No. 2, Jan. 11, 2011, pp. 510-515.
Jaipuri et al., "Synthesis and Quantitative Evaluation of Glycero-D-manno-heptose Binding to Concanavalin A by Fluorous-Tag Assistance", Angewandte Chemie International Edition, vol. 47, No. 9, Jan. 18, 2008, pp. 1707-1710.
Sherratt et al., "Copper-catalysed cycloaddition reactions of nitrones and alkynes for bioorthogonal labelling of living cells", RSC Adv., vol. 4, No. 87, Jan. 1, 2014, pp. 46966-46969.
Sadamoto, Reiko et al., "Bacterial Surface Engineering Utilizing Glucosamine Phosphate Derivatives as Cell Wall Precursor Surrogates," Chemistry, A European Journal, 14:10192-10195 (2008).
Smellie et al., "Synthesis of putative chain terminators of mycobacterial arabinan biosynthesis," Organic & Biomolecular Chemistry, 5:2257-2266 (2007).
Voisin et al., "Glycosylation of Pseudomonas aeruginosa Strain Pa5196 IV Pilins with Mycobacterium-Like α-1,5-Linked D-Araf Oligosaccharides," Journal of Bacteriology, vol. 189, No. 1, pp. 151-159 (2007).

* cited by examiner

METHOD FOR LABELING SPECIFICALLY LIVING MICROORGANISMS COMPRISING THE USE OF MODIFIED MONOSACCHARIDE COMPOUNDS

This application is the U.S. national phase of International Application No. PCT/EP2016/059864 filed May 3, 2016, which designated the U.S. and claims priority to EP Patent Application No. 15166249.1 filed May 4, 2015, the entire contents of each of which are hereby incorporated by reference.

The present invention concerns a method for labeling of living microorganisms, in incorporating a compound residue bearing a reactive group into said microorganisms, preferably at the surface thereof, more particularly in the envelope thereof especially when said microorganisms are bacteria.

The term "living microorganism" comprises any unicellular organism capable to multiply under culture conditions, more particularly prokaryotic and unicellular eukaryotic microorganisms.

The prokaryotic microorganisms comprise bacteria (also called Eubacteria) as well as Archaea (also called archeabacteria).

The bacteria comprise Gram positive bacteria and Gram negative bacteria as well as bacteria which are neither Gram negative nor Gram positive.

The unicellular eukaryotic microorganisms comprise unicellular Fungi (including especially yeasts), amoebas and unicellular Protista.

The present invention provides more particularly a method allowing labeling of microorganisms comprising bacteria as well as unicellular Fungi and amoebas.

The term «envelope» herein includes any wall, layer or membrane at the surface of the microorganism, especially cellular wall of the microorganism, the envelope including more particularly the inner plasma membrane and the peptidoglycan layer for the bacteria as well as the outer membrane for Gram negative bacteria.

WO 2013/107759 discloses a method of labeling living bacteria, more particularly, Gram negative bacteria. The method essentially consists in incorporating in the membrane of said bacteria by assimilation an analog of endogenous monosaccharide compound of the ulosonic acid type modified so that it bears a so-called first reactive chemical function such as azide (—N3) or alkyne (—C≡CH) group thus enabling a reaction of this first reactive group with a molecule bearing the complementary reactive group especially through a so-called click chemistry reaction.

More particularly, it has been disclosed in WO 2013/107759 that such modified analogs of endogenous sugars comprising ulosonic acid or ulosonate residue are particularly advantageous in that such residues can be found in glycans of the bacterial membrane, especially LPS of all of the Gram negative bacteria, and moreover they can be directly assimilated in the same form into which they will be incorporated in the said glycans of the LPS of Gram negative bacteria.

Ulosonic acids (also called ketoaldonic acids, or aldulosonic acids) are monosaccharides of the ketose family, presenting a ketone function at C-2, and a carboxylic acid at C-1. Octulosonic and nonulosonic acids are found in diverse natural glycans, including different forms of bacterial glycans (especially LPS, capsular polysaccharide, glycoproteins). The biosynthetic pathway leading to the elaboration of these glycans generally involves the free ulosonic acid as an intermediate, which is then directly activated in the form of a CMP-sugar donor. All of the Gram negative bacteria LPS comprise a said ulosonate residues.

More accurately, the method disclosed in WO 2013/107759 is a method for specifically labeling living bacteria of a given category of bacteria in a sample comprising bacteria, the method comprising the steps of:
a) incubating said bacteria of said sample with at least one analog of a monosaccharide compound, said monosaccharide being an endogenous monosaccharide residue of glycans of the outer membrane of such given category of bacteria, the said endogenous monosaccharide residue comprising an ulosonic acid or ulosonate salt residue, the said analog of a monosaccharide compound being a modified monosaccharide substituted at a given position by a first reactive chemical group capable to react with a second reactive group of a labeling molecule, and
b) contacting said bacteria with a said labeling molecule comprising a said second reactive group, for generating the reaction of said first reactive group of said analog residue incorporated within said glycans of the outer membrane of said living bacteria with said second reactive group of said labeling molecule.

Particularly, in WO 2013/107759 the said analog monosaccharide is a substituted ulosonic acid having one of the following formula (I″) or an ulosonate salt thereof:

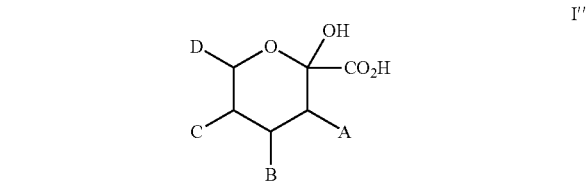

Wherein
A, B and C can be independently H, OH, NH$_2$, OH and NH$_2$ being substituted or not by protecting groups thereof, and
D is an alkyl chain in C$_2$ to C$_4$, and
at least one of A, B, C or D groups is substituted by a said first reactive group.

In WO 2013/107759, the said analog of monosaccharide incubated with the living bacteria in step a) and then incorporated within its outer membrane after assimilation by the bacteria, can be identical to the endogenous monosaccharide incorporated in the glycans chain of the outer membrane except it is modified only by substitution of the said first reactive group.

The goal of the present invention was to find out other monosaccharidic compounds capable to be assimilated within a broad range of unicellular microorganisms especially a broader range of bacteria and especially within both Gram negative and Gram positive bacteria as well as unicellular eukaryotic microorganisms, such as unicellular Fungi, amoebas and unicellular Protista, and presenting advantageous and different properties as to their specificity of incorporation in respect to the concerned category of microorganism.

More accurately, the present invention provides a method for labeling specifically living microorganisms in a sample comprising microorganisms, the method comprising the steps of:
a) incubating said microorganisms of said sample with at least one modified monosaccharide compound comprising a first reactive chemical group capable to chemically react with a second reactive group, so that a residue bearing said first reactive group is incorporated into said living microorganisms, preferably at the surface of said microorganisms, especially incorporated into the envelop of said microorganism, and b) contacting said residue incorporated into said living microorganism, with a labeling molecule comprising a said second reactive group, for generating the chemical reaction of said first reactive group of said residue incorporated into said living microorganism with said second reactive group of said labeling molecule, resulting in a covalent link, characterized in that the said modified monosaccharide compound has the following formula (I'), or a salt thereof:

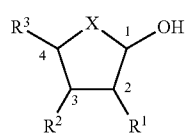

X can be O, NH or S, preferably O and NH, and

R1 and R2 can be independently H, OH, $NH_2$, OH and $NH_2$ being substituted or not by protecting groups thereof, preferably substituted by alkyl, hydroxyalkyl, acyl, formyl or imidoyl groups, and R3 is H or an alkyl chain in $C_1$ to $C_4$, each carbon being substituted or not substituted by OH or $NH_2$ substituted or not by protecting groups thereof, preferably by alkyl, hydroxyalkyl, acyl, formyl or imidoyl groups, and at least one of X, R1, R2 and R3 groups, preferably R3, being substituted by a said first reactive group Ra.

Accordingly, the above defined compound of formula I' don't comprise a carboxylic acid group (—CO2H) at the position C-1 of the cycle of the formula I' contrary to the compounds of formula I" and corresponding formula II in equilibrium of WO 2013/107759.

Such compound of formula (I') can be assimilated by a broad range of category of living microorganisms including especially unicellular prokaryotic microorganisms comprising Archaea and bacteria and unicellular eukaryotic organisms comprising more particularly unicellular Fungi (including interalia yeasts), amoebas and unicellular Protista.

According to the present invention, the accurate mechanisms by which said modified monosaccharide bearing said first reactive group is assimilated by the microorganism in incorporating said residue therein is not quite determined.

However, it appears that said monosaccharide compound can be different than endogenous monosaccharides residues of said microorganism, especially different than endogenous monosaccharides residues of the envelope of said microorganism and more particularly, in the case of Gram negative bacteria different than endogenous monosaccharides residues of polysaccharides of the outer membrane of such bacteria, such as LPS or capsular polysaccharide (CPS) of bacteria, and then being nevertheless capable to penetrate and be incorporated into said microorganism.

The expression "endogenous monosaccharide residue" means a residue, naturally present in said microorganisms, especially in the envelope of said microorganisms, more particularly the envelope of said bacteria.

According to the present invention, the said monosaccharide compounds being modified by the said first reactive group might comprise analogs of precursors of endogenous monosaccharides in the biosynthetic pathway thereof in said microorganisms and especially in the envelope of said microorganism, more particularly the envelope of said bacteria.

More particularly, the part of the monosaccharide compound of the present invention onto which the said first reactive group is substituted, is different than the endogenous monosaccharide residue incorporated in said microorganism, especially different than the endogenous monosaccharide residue incorporated in the glycans of the envelop of said bacteria, but it might be metabolized in a modified monosaccharide residue incorporated in the glycans of the envelope of said bacteria, said monosaccharide being modified by said first reactive group.

More particularly, in the method of the present invention, said modified monosaccharide compounds can be analogs of precursors of modified endogenous monosaccharides of bacteria of the above formula (I') disclosed and claimed in WO 2013/107759. The compounds of the present invention can be metabolized and converted during the incubation step a) so as to become assimilated by said bacteria, likely incorporated within glycans of the envelope of said bacteria, namely incorporated as modified monosaccharides residues of the glycans of the envelope of such bacteria, namely monosaccharides residues modified in that they bear the said first reactive groups.

More particularly, said incorporated residue can be a monosaccharide residue. However, alternatively, it might be that said modified monosaccharide compounds can be converted, metabolized or degraded in a molecule giving rise to said residue other than a monosaccharide residue incorporated into said microorganism or give rise to a precursor of said residue.

The furanosic cycle (I') ca be in part in equilibrium with the following pyranosic compound (II') although in practice the said reactive group Ra prevents the formation of the pyranosic cycle:

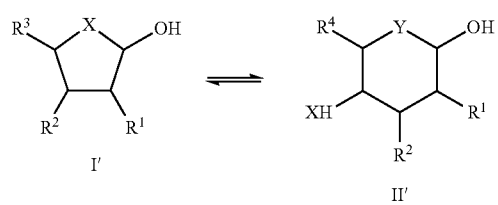

Wherein in compounds (I') and (II'), X, R1, R2 and R3 are such above defined, Y=O or NH and R4 is H or an alkyl chain in $C_1$ to $C_3$ such that R3=CHYHR4 each carbon being substituted or not substituted by OH or $NH_2$ substituted or not by protecting groups thereof, preferably by alkyl, hydroxyalkyl, acyl, formyl or imidoyl groups.

More particularly, in compound of formula (I') when R3 is an alkyl chain in $C_1$ to $C_4$, R3 is other than CHYHR4, compound (I') being then therefore not in equilibrium with (II').

Preferably, the said modified monosaccharide compound is a stereoisomer having the formula (I) or a salt thereof

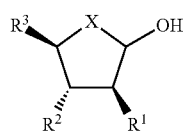

Preferably, the said modified monosaccharide compound is a compound having the formula (I) or (I') or a salt thereof wherein:

X is O, and

R1 is H, OH, NH$_2$, OH and NH$_2$ being substituted or not by said protecting group, and R2 is H, OH, NH$_2$, OH and NH$_2$ being substituted or not by said protecting group, and;

at least R1, R2 or R3 being substituted by a said first reactive group Ra.

More particularly, the said modified monosaccharide compound is a compound having the following formula, or a salt thereof wherein:

R1 and R2 are OH, OH being substituted or not by a protecting group, and

R3 is —CH$_3$, —CH$_2$OH or —CH$_2$NH$_2$, preferably —CH$_3$ or —CH$_2$NH$_2$ these groups being substituted by said first reactive group Ra.

More preferably, said modified monosaccharide compound is a compound having the following stereoisomer formula (Ia) (so-called herein after "Ara-N$_3$"), or a salt thereof wherein:

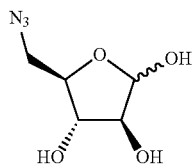

More particularly, for OH the protecting group can be preferably an alkyl, hydroxyalkyl, acyl or formyl group.

More particularly, for NH$_2$ the protecting groups can be selected among alkyl, hydroxyalkyl, acyl, formyl or imidoyl groups.

NH$_2$ can be protected by one or two protecting groups, especially one CH$_3$ group and one alkyl, hydroxyalkyl, acyl, formyl or imidoyl group, especially acetyl (Ac), acetimidoyl (Am), N-methyl-acetimidoyl, N,N-dimethyl-acetimidoyl, formyl (Fo), or hydroxybutanoyl group.

The said monosaccharide residue of said modified monosaccharide compound (Ia) is an arabinose analog of the natural precursor arabinose 5-P (A5P) this latter being a precursor of the endogenous monosaccharide residue so-called Kdo (I-1') in the biosynthetic pathway thereof in a great number of bacteria as shown in the pathway of FIG. 1B of WO 2013/107759. In the biosynthetic pathway of Kdo in Bacteria wherein arabinose-5-P is converted into Kdo-8-P which becomes Kdo, enzyme Kdo-8-phosphate (Kdo-8-P) synthase converts arabinose-5-Phosphate into Kdo-8-P and enzyme Kdo-8-P phosphatase converts OPO$_3^{2-}$ group of the Kdo-8-P into hydroxy (OH) to yield Kdo.

It is therefore likely that compound (Ia) might be converted into a modified endogenous Kdo-N$_3$ of the following formula (I-1):

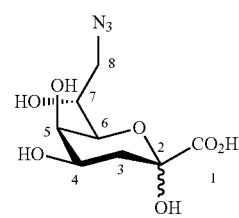

More generally, compounds of formula (I) and (I') might be analogs of precursors of endogenous compounds of formula (I'') of the outer membrane in bacteria as disclosed in WO 2013/107759:

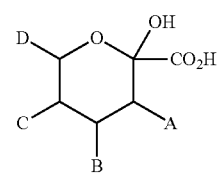

As per the conventional representation of formula, the carbon atoms in the positions C-1 to C-n of the various above cycles and substituents H bound to these carbon atoms are not represented.

The said chemical reaction between said first and second reactive groups results in a covalent link which in few examples can be a covalent coordination link in a metallic complex coordinated with ligands.

Preferably, the said first reactive group Ra is selected among groups consisting in or bearing the group azido (—N$_3$) and groups consisting in or bearing the group alkyne (—C≡C—), the said first reactive group being preferably the group azido, and the said second reactive group is selected among groups consisting in or bearing respectively the groups alkyne and azido, the said second reactive group being preferably the group alkyne, and reacting the said azido reactive group with the said alkyne reactive group is carried out in performing an azide alkyne cycloaddition.

More preferably, Ra is —N3 or —C≡CH, preferably —N$_3$.

The compound of formula (I) and (I') can be used for labeling living microorganisms including especially unicellular prokaryotic microorganisms comprising Archaea and bacteria and unicellular eukaryotic microorganisms comprising more particularly unicellular Fungi (including especially yeasts) and unicellular Protista.

More particularly, the compound of formula (I) and (I') can be used for labeling all kind of bacteria including Gram negative or positive bacteria as well as unicellular Fung.

More particularly, the compounds of formula (I) and (I') can be used for labeling Gram negative as well as Gram positive bacteria which can be selected among interalia in the following genus of bacteria for example:

a) Gram negative bacteria: *Acinetobacter, Bacteroides, Bartonella, Bordetella, Brachyspira, Brucella, Burkholderia, Chlamydophila, Coxiella, Chryseobacterium, Cronobacter, Clostridium, Campylobacter, Escherichia, Francisella, Cardiobacterium, Edwardsiella, Ehrlichia, Eikenella, Elizabethkingia, Enterobacter, Fusobacterium, Haemophilus, Helicobacter, Klebsiella, Legionella, Leptospira, Morganella, Myxococ-* cus, Neisseria, Neonickettsia, Pasteurella, Plesiomonas, Porphyromonas, Prevotella, Proteus, Providencia, Pseudoalteromonas, Pseudomonas, Rickettsia, Rhodocyccius, Salmonella, Serratia, Sinorhizobium, Shigella, Schewanella, Shewamma, Stenotrophomonas, Yersinia, Streptobacillus, Tenadbaculum, Treponema, Vibrio, and b) Gram positive bacteria: *Bacillus, Kocuria, Enterococcus, Lactococcus, Lactobacillus, Listeria, Micrococcus, Staphylococcus, Streptococcus.*

Among the Gram negative bacteria which can assimilate compounds of formula (I) and (I'), preferably (Ia), the following species can be cited: *Acinetobacter baumannii, Cronobacter sakazakii, Escherichia coli, Klebsiella pneumoniae, Legionella pneumophila, Neisseria gonorrhoeae, Neisseria meningitidis, Proteus mirabilis, Providentia stuartii, Pseudomonas fluorescens, Salmonella typhimurium, Serratia marcescens, Stenotrophomonas maltophilia, Vibrio cholerae*

More particularly, among the Gram positive bacteria which can assimilate compounds of formula (I) and (I'), preferably (Ia), the following species can be cited: *Bacillus subtilis, Bacillus cereus, Enterococcus durans, Enterococcus faecalis, Listeria monocytogenes, Micrococcus luteus, Staphylococcus aureus, Staphylococcus aureus aureus, Staphylococcus epidermis, Staphylococcus saprophyticus, Streptococcus agalactiae.*

More particularly, the compound of formula (I) and (I') can be used for labeling fungi which can be selected among interalia in the following genus for example: *Aspergillus, Candida, Fusarium* and *Geotrichum* and amoebas of the genus *Acanthamoebae*.

More particularly, said compound of formula (I) and (I'), preferably (Ia) can be assimilated especially, in the following species of fungi and yeast: *Aspergillus niger, Candida albicans* and *Geotrichum candidum* and following species of amoebas *Acanthamoebae castellanii*.

Among the above microorganisms, the following bacteria did not assimilate Kdo-N$_3$ (I-1') of WO 2013/107759: *Bacillus subtilis, Neisseria gonorrhoeae, Enterococcus faecalis, Listeria monocytogenes, Micrococcus luteus, Staphylococcus aureus, Staphylococcus aureus aureus, Staphylococcus epidermis*, as well as the following Fungi: *Aspergillus niger, Candida albicans, Fusarium, Geotrichum candidum* and the amoeba *Acanthamoebae castellanii*.

More particularly, the incubation time at step a) will depend on the microorganism doubling time, the incubation time being more particularly from 1 hr to 72 hr, more particularly from 1 hour to 36 hr and the modified monosaccharide compound concentration is from $10^{-5}$ M to 1 M, for detecting a microorganism concentration preferably of no more than $10^{11}$ cell/ml, more particularly no more than $10^9$ cell/mi.

As most of the sanitary regulations refer to the numbering of microorganisms capable to multiply, especially capable to multiply on a solid or in liquid growth medium, advantageously, the present invention provides more particularly a method for labeling specifically microorganisms capable of multiplying wherein said microorganisms are incubated in a culture medium in (liquid medium) or on (solid medium) which said microorganisms are capable to multiply.

Severe pathogens are hiding amongst above mentioned microorganisms, and the rapid labelling and/or detection of living microorganisms represents a major sanitary challenge. The modified monosaccharides of the present invention are rapidly assimilated by the microorganisms and enable fast labeling and detection thereof—the overall process taking less than one day, of living wild type microorganisms. This method is very rapid in comparison to usual detection of living microorganism which needs normally between 2 days and more than one month depending on the microorganism strain.

Advantageously, the present invention comprises the further step (c) of detecting living microorganism in detecting whether said microorganism comprise said labeling molecule bound to said living microorganism and/or immobilizing said living microorganism bearing said labeling molecule onto a solid substrate, wherein said labeling molecule is a molecule comprising a detectable substance or capable to react or to be bound to a detectable substance or said labeling molecule is a first molecule bearing a said second reactive group, said first molecule being capable to react or to be bound to a second molecule and/or to a solid substrate, preferably said second molecule comprising a detectable substance and/or said second molecule being bound or capable to be bound to a said solid substrate.

Accordingly, the present invention enables (a) labeling of living microorganism as well as (b) numbering or detection of living microorganism as well as (c) concentrating and/or isolating living microorganism immobilized on a solid support; especially with a solid support constituted of magnetic beads bearing the said second reactive group.

More particularly, said labeling molecule is a detectable molecule comprising a detectable substance, the method comprising the step c) of detecting living microorganism in detecting whether said microorganism comprise said detectable molecule bound to said microorganism.

The said detecting step c) can be carried out in a liquid medium or on a solid substrate.

More particularly, said labeling molecule can be a detectable molecule, namely a molecule consisting in or bearing a detectable substance, namely a substance capable to be detected by techniques known by one skilled in the art, such as fluorescence, colorimetry or luminescence.

More particularly, said labeling molecule is a first ligand or first binding protein bearing a said second reactive group and in step c) said living microorganism coupled to said first ligand or first binding protein is detected and/or immobilized by contacting said first ligand or first binding protein with a second ligand or second binding protein reacting or binding specifically to said first ligand or first binding protein.

More particularly, said labeling molecule is a first ligand, preferably biotin, bearing a said second reactive group, and in step c) said living microorganism coupled to said first ligand are detected by reaction of said microorganism with an antibody or another protein specific to said first ligand, said antibody bearing a detectable substance, preferably a fluorochrome or luminescent molecule or an enzyme.

The present invention provides also a kit for carrying out the method of the present invention comprising:
- a said modified monosaccharide compound of formula (I) and
- a said labeling molecule comprising a said second reactive group capable of reacting with said first reactive group, and
- if required, reactants for generating the reaction of said first reactive group with said second reactive group of said labeling molecule, and
- preferably, a culture or incubation medium allowing the growth of a said microorganism, preferably specific to the growth of said microorganism.

Preferably, the said first reactive group Ra is selected among groups consisting in or bearing the group azido (—N$_3$) and groups consisting in or bearing the group alkyne (—C≡C—), and the said second reactive group Rb is selected among groups consisting in or bearing respectively the groups alkyne (—C≡C—) and azido (—$N_3$), and reacting the said azido reactive group with a said alkyne group (—C≡C—) is carried out in performing an azide alkyne cycloaddition.

An azide alkyne cycloaddition is a well-known so-called click chemistry reaction in the presence or not of a copper catalyst wherein the azide group reacts with the alkyne group to afford a triazole. More particularly, the reaction can be carried out in copper catalyzed conditions in the presence of a tris-triazolyl ligand, preferably TGTA. More particularly, the detectable molecule is a fluorochrome bearing a terminal alkyne group.

More particularly, the reaction can be carried out in the presence of a tris-triazole ligand such as TGTA (Tris((1-(β-D-glucopyranosyl)-1H-[1,2,3]-triazol-4-yl)methyl)amine) or TBTA (Tris-[(1-benzyl-1H-1,2,3-triazol-4-yl) methyl] amine) and an Alexa labeling molecule bearing a terminal alkyne group with a catalyst so as to perform an azide alkyne cycloaddition of the said fluorochrome and said analog compound of formula (I).

Other appropriate ligands frequently used are: tris(3-hydroxypropyltriazolylmethyl)amine (THPTA), 2-(4-((bis ((1-tert-butyl-1H-1,2,3-triazol-4-yl)methyl)amino)methyl)-1H-1,2,3-triazol-1-yl)ethanesulfonic acid (BTTES), tris((1-((O-ethyl) carboxymethyl)-(1,2,3-triazol-4-yl)) methyl) amine, bathophenanthroline disulfonate, or tris(2-benzimidazolylmethyl)amines.

Alternatively, azide alkyne cycloaddition can be performed in the absence of copper, if a strained alkyne is used, such as azadibenzocyclooctyne (ADIBO, DIBAC or DBCO) or tetramethoxydibenzocyclooctyne (TMDIBO).

Other appropriate strained alkynes frequently used for copper-free reaction include: cyclooctyne (OCT), aryl-less cyclooctyne (ALO), monofluorocyclooctyne (MOFO), difluorocyclooctyne (DIFO), dibenzocyclooctyne (DIBO), dimethoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dibenzocyclooctyne (ODIBO), carboxymethylmonobenzocyclooctyne (COMBO), or benzocyclononyne.

Other reactive groups and other reactions are possible such as: Staudinger Ligation (first reactive group=azide and second reactive group=phosphine), copper-free click-chemistry (first reactive group=azide and second reactive group=constrained alkyne (intracyclic alkyne)), carbonyl condensation (first reactive group=aldehyde or ketone and second reactive group=hydrazide or oxyamine), thiol-ene click chemistry (first reactive group=thiol and second reactive group=alkene), nitrile-oxide-ene click chemistry (first reactive group=nitrile oxide or aldehyde, oxime, or hydroxymoyl chloride or chlororoxime and second reactive group=alkene or alkyne), nitrile imine-ene click chemistry (first reactive group=nitrile imine or aldehyde, hydrazone, or hydrazonoyl chloride or chlorohydrazone and second reactive group=alkene or alkyne), inverse electron demand Diels-Aider ligation (first reactive group=alkene and second reactive group=tetrazine), isonitrile-tetrazine click chemistry (first reactive group=isonitrile and second reactive group=tetrazine), Suzuki-Miyaura coupling (first reactive group=aryl halide and second reactive group=aryl boronate), His-tag (first reactive group=oligo-histidine and second reactive group=nickel-complex or nickel ligand).

In the above-mentioned listing of groups involved in the reactions, the first reactive group and the second reactive group can be permuted. All the above mentioned chemical reactions result in a covalent link.

Other and higher specificity of detection can be obtained in incubating the microorganisms sample with two said different modified monosaccharide compounds and two different detectable molecules.

In another particular embodiment of the method of the present invention, the said incubation of step a) and reaction of step b) are carried out on a membrane filter so that the cultivated microorganism emanating from a same original microorganism which has been multiplied are grouped together and can be visualized with a microscope and the said detectable molecule can be detected by visualization with a said microscope. Therefore, the number of cultivable microorganism can be quantified thereby.

This embodiment enables to filter the tested sample on said membrane filter such as a polyester membrane, prior to assimilation of the said modified monosaccharide to avoid over-estimation of living microorganism due to possible growth during the assimilation period. Indeed, when cells fixed on the top of such membrane start to grow, they stay together and form a micro-colony that can be easily detected as coming from the same single cell. Therefore, this enables to number by counting the cultivable microorganism.

The present invention also provides a kit for carrying out the method of the invention further comprising a culture or incubation medium allowing the growth of a said microorganism.

Preferably, the said culture or incubation medium further comprises agents enhancing and/or accelerating the growth speed and/or the capacity to form colonies of the said given category of microorganism. More particularly, the incubation medium comprises at least an antioxidant agent such as pyruvate or catalase.

More particularly, in one embodiment, the kit further comprises:
a said detectable molecule or said second molecule bearing a detectable substance, preferably a fluorochrome or luminescent molecule or an enzyme, and/or
a solid substrate bearing a said second molecule capable of specifically reacting or binding with said labeling molecule.

More particularly, in one embodiment, the kit of the present invention further comprises:
a said detectable molecule comprising a said second reactive group capable of reacting with said first reactive group, and
a solid medium allowing visualization of the microorganism after incubating with the said modified monosaccharide compound, said reactants and said detectable molecule.

More particularly again, the kit comprises:
a said modified monosaccharide compound substituted by a said first reactive group comprising an azido or alkyne group, and
a said second reactive group of the detectable molecule bearing an alkyne or, respectively, azido group, and
possibly, said reactants comprising a copper catalyst and a tristriazolyl ligand. In
a first particular embodiment, said labeling molecule can be a detectable molecule, namely a molecule consisting in or bearing a detectable substance, namely a substance capable to be detected such as a fluorochrome or luminescent substance or an enzyme such as peroxidase, said enzyme being more particularly detected after reacting with a co-reactant.

In a further particular embodiment, useful for isolating and/or concentrating living microorganism, the said labeling molecule can be bound to a solid substrate when carrying out step b).

In a further particular embodiment, said labeling molecule is a molecule which is a first ligand or first binding protein bearing a said second reactive group and in step c) said living microorganism coupled to said first ligand or first binding protein is detected and/or immobilized by contacting said first ligand or first binding protein with a second molecule which is a second ligand or second binding protein reacting or binding specifically to said first ligand or first binding protein.

Then, advantageously, said first or second ligand or binding protein can react or be bound to a third binding protein bearing a said detectable substance such as a fluorochrome or luminescent substance or an enzyme such as peroxidase, said third binding protein binding specifically to a said first and/or second ligand or binding protein. Detecting said detectable substance via a said second ligand or second binding protein or third binding protein enables to amplify the signal of the said detectable substance.

More particularly, the first ligand or first binding protein can be:
- biotin, said second binding protein being then avidin or streptavidin and said third binding protein being an antibody raised against biotin, or
- avidin or streptavidin, said second ligand binding protein being then biotin and said third binding protein being an antibody raised against avidin or streptavidin, or
- a first antibody, said second binding protein being then a second antibody specific to said first antibody and said third binding protein being a third antibody specific to said first antibody.

More particularly, said labeling molecule is a first ligand, preferably biotin, bearing a said second reactive group, and in step c) said living microorganism coupled to said first ligand are detected by reaction of said microorganism with an antibody specific to said first ligand, said antibody bearing a detectable substance, preferably a fluorochrome or luminescent molecule or an enzyme.

More particularly again, said labeling molecule is a first ligand, preferably biotin, bearing a said second reactive group, and in step c) said living microorganism coupled to said first binding protein is immobilized by reacting said first ligand with a solid substrate, preferably magnetic beads, coupled to a said second binding protein, preferably avidin or streptavidin, before detecting said living microorganism by bacterial DNA enzymatic amplification or by reaction of said bacteria with a third binding protein reacting or binding specifically to said first ligand or second binding protein, said third binding protein bearing a detectable substance, preferably a fluorochrome or luminescent molecule or an enzyme, said third binding protein being preferably an antibody specific to said first ligand or first binding protein.

In one embodiment, more particularly, the labeling molecule can be an enzyme bearing the second reactive group such as a horseradish peroxidase (HRP) or an urease enzyme.

Such embodiment wherein said living microorganisms are immobilized on said solid substrate enables to concentrate the sample into said microorganism and to quantify said living microorganism by any known method including DNA enzymatic amplification such as PCR, especially Real Time PCR or a method involving immunological reaction with a labeled antibody such as an ELISA test.

Other characteristics and advantages of the present invention will be more apparent in the light of the following detailed description and examples of illustrative and non-limitative embodiments.

EXAMPLE 1: SYNTHESIS OF COMPOUND (IA): ARA-$N_3$

In the synthesis the following reagents and conditions have been used: (i) TsCl, pyridine. (ii) pyridine, $Ac_2O$. (iii) $NaN_3$, DMF. (iv) $CH_3ONa$, $CH_3OH$.

Thin layer chromatography was performed over Merck 60 F254 with detection by UV, and/or by charring with sulphuric acid or KMnO4 or phosphomolybdic acid solutions. Silica gel 60 40-63 µm was used for flash column chromatography.

NMR spectra were taken on Bruker Avance 300 or 500 MHz spectrometers, using the residual protonated solvent as internal standard. Chemical shifts δ are given in parts per million (ppm) and coupling constants are reported as Hertz (Hz). Splitting patterns are designated as singlet (s), doublet (d), triplet (t), doublet of doublet (dd), doublet of doublet of doublet (ddd). Splitting patterns that could not be interpreted or easily visualized are designated as multiplet (m).

Mass spectra were taken on a Thermo Scientific TSQ or on a Bruker micrOTOFq or on a Waters LCT Premier XE (ToF), with electrospray ionization in the positive (ESI+) mode of detection.

IR-FT spectra were recorded on a Perkin Elmer Spectrum 100 spectrometer. Characteristic absorptions are reported in $cm^{-1}$.

Specific optical rotations were measured at 20° C. with an Anton Paar MCP 300 polarimeter in a 10-cm cell at 20° C. and 589 nm.

Compound (Ia) was the compound (5) in the following scheme 1 showing the various compounds involved in the steps of the synthesis thereof.

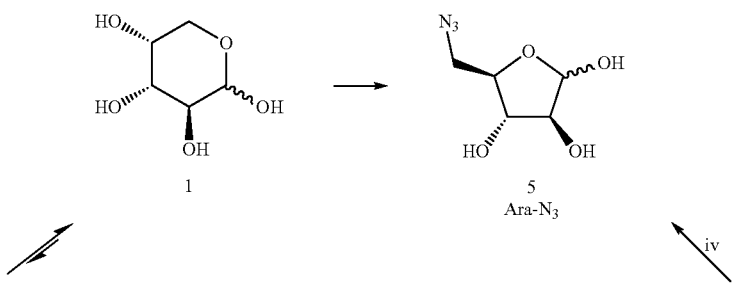

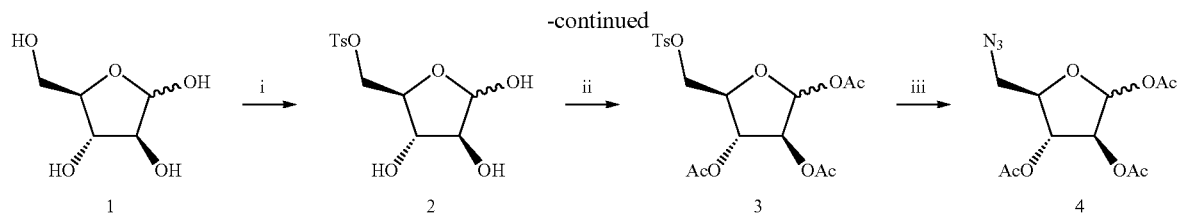

The reagents and conditions in the various steps are: (i) TsCl (1.1 eq.), pyridine (1.0 M), 100° C.→r. t., 18 h. (ii) pyridine/Ac$_2$O (2:1, 0.7 M), 18 h. (iii) NaN$_3$ (2.0 eq.), DMF (0.4 M), 80° C., 20 h, 15% over 3 steps. (iv) CH$_3$ONa (0.1 eq.), CH$_3$OH (0.2 M), r. t., 3 h, 99%

1) Preparation of 5-azido-5-deoxy-1,2,3-tri-O-acetyl-D-arabinofuranose (4)

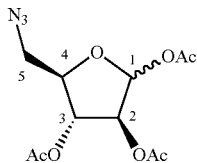 [SMILES: CC(=O)OC1O[C@H](CN=[N+]=[N-])[C@@H](OC(C)=O)[C@@H]1OC(C)=O]

Commercial D-arabinose (1) (6.00 g, 40 mmol) was heated at 100° C. for 2 hours in pyridine (40 mL). The solution was allowed to cool down, further treated with tosyl chloride (8.38 g, 44 mmol, 1.1 equiv.), and stirred for 16 hours at room temperature (2), not isolated). Acetic anhydride (20 mL) was then added. After complete acetylation, as determined by TLC, solvents were evaporated, and residual traces were co-evaporated several times with toluene (3), not isolated). The residue was dissolved in DMF (100 mL), sodium azide (5.20 g, 80 mmol, 2.0 eq.) was added, and the suspension was heated at 80° C. for 20 hours. After dilution with ethyl acetate and washing with water, the organic layer was dried over anhydrous magnesium sulfate and concentrated. The residue was purified by flash chromatography (petroleum ether/ethyl acetate 7:3). The first eluted product was determined to be the expected 5-azido-1,2,3-tri-O-acetyl-D-arabinofuranose (4) (1.83 g, 15%, α/β~2:1).

$^1$H-NMR (360 MHz, CDCl$_3$) δ (ppm): 6.41 (d, 0.33H, J$_{1,2}$ 3.5 Hz, H-1 β); 6.23 (d, 0.67H, J$_{1,2}$~1 Hz, H-1α); 5.40-5.37 (m, 1.34H, H-2β, H-3β); 5.23 (d, 0.67H, J$_{1,2}$~Hz, H-2α); 5.06 (d, 0.67H, J$_{3,4}$ 4.6 Hz, H-3α); 4.30 (ddd, 0.67H, H-4α); 4.16-4.10 (m, 0.33H, H-4β); 3.69 (dd, 0.67H, J$_{5a,5b}$ 13.5, J$_{4,5a}$ 3.1 Hz, H-5aα); 3.61 (dd, 0.33H, J$_{5a,5b}$ 13.1, Asa 3.6 Hz, H-Sa); 3.51-3.43 (m, 1H, H-Sba, H-Sb); 2.15, 2.13, 2.12, 2.11, 2.11, 2.09 (6s, 18H, 6 CH$_3$CO).

$^{13}$C-NMR (62.5 MHz, CDCl$_3$) δ (ppm): 170.3, 170.0, 169.1 (3 C=O); 99.2 (C-1α); 93.5 (C-1β); 84.1 (C-4α); 80.8 (C-4β); 80.6 (C-3α); 77.4 (C-2α); 75.1 (C-2β); 74.8 (C-3β); 53.0 (C-5β); 51.3 (C-5α); 20.9, 20.6, 20.3 (3 CH$_3$).

LRMS (ESI+): [M+H]$^+$ 324.0.

HRMS (ESI+): [M+H]$^+$ (C$_{11}$H$_{15}$N$_3$NaO$_7$) Calc. m/z: 324.0802, found: 324.0802.

2) Preparation of 5-Azido-5-deoxy-D-arabinofuranose (5)

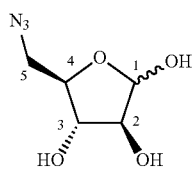 [SMILES: [N-]=[N+]=NC[C@H]1OC(O)[C@@H](O)[C@@H]1O]

Protected 5-azido-1,2,3-tri-O-acetyl-D-arabinose (4) was then dissolved into anhydrous methanol (30 mL), treated with a methanolic solution of CH$_3$ONa (0.2 mol·L$^{-1}$, 3 mL) and stirred at room temperature for 3 hours under an argon atmosphere. After neutralization (Dowex® 50 (H$^+$)) filtration, and concentration, 5-azido-5-deoxy-D-arabinofuranose (5) was obtained in 99% yield (1.03 g).

Rf (dichloromethane/methanol 92:8): 0.28.

IR (cm$^{-1}$): 3367, 2106, 1281, 1040.

HRMS (ESI$^+$): [M+H—N$_2$]$^+$ (C$_5$H$_{10}$NO$_4$) Calc. m/z: 148.0604, found: 148.0610.

Anomer Alpha (5α):

$^1$H-NMR (500 MHz, D$_2$O) δ (ppm): 5.24 (d, 1H, J$_{1,2}$ 2.9 Hz, H-1); 4.17 (ddd, 1H, J$_{3,4}$ 6.4, J$_{4,5b}$ 5.8, J$_{4,5a}$ 3.5 Hz, H-4); 4.01 (dd, 1H, J$_{2,3}$ 4.6, J$_{1,2}$ 2.9 Hz, H-2); 3.97 (dd, 1H, J$_{3,4}$ 6.4, J$_{3,2}$ 4.6 Hz, H-3); 3.64 (dd, 1H, J$_{5a,5b}$ 13.6, J$_{4,5a}$ 3.5 Hz, H-5a); 3.44 (dd, 1H, J$_{5a,5b}$ 13.6, J$_{4,5b}$ 5.8 Hz, H-5b).

$^{13}$C-NMR (125 MHz, D$_2$O) δ (ppm): 101.0 (C-1); 81.3 (C-4); 81.2 (C-2); 76.3 (C-3); 51.5 (C-5).

Anomer Beta (5 β):

$^1$H-NMR (500 MHz, D20) δ (ppm): 5.28 (br d, 1H, J$_{1,2}$ 3.1 Hz, H-1); 4.10-4.05 (m, 2H, H-2, H-3); 3.89 (ddd, 1H, J$_{3,4}$ 7.1, J$_{4,5b}$ 6.5, J$_{4,5a}$ 3.5 Hz, H-4); 3.59 (dd, 1H, J$_{5a,5b}$ 13.3, J$_{4,5a}$ 3.5 Hz, H-5a); 3.42 (dd, 1H, J$_{5a,5b}$ 13.3, J$_{4,5b}$ 6.5 Hz, H-5b).

$^{13}$C-NMR (125 MHz, D$_2$O) δ (ppm): 95.2 (C-1); 79.6 (C-4); 75.8 (C-2); 74.7 (C-3); 52.6 (C-5).

EXAMPLE 2: COMPARISON OF LABELING OF LIVING MICROORGANISMS WITH COMPOUNDS

Ara-N$_3$ (Ia) of the present invention and compound Kdo-N$_3$ (I-1) of the prior art.

1) Material and Methods.

1.1) Microorganism Strains and Growth Conditions.

The bacteria and fungi strains listed in tables 1 and 3 are grown in the culture media and conditions listed in Tables 1 and 2. All strains were grown in a rotary shaker (160 rpm) at 30 or 37° C.

TABLE 1

| microorganisms | REFERENCES | Growth conditions |
|---|---|---|
| BACTERIA | | |
| *Acinetobacter baumannii* | ATCC 17978 | LB-24 H-37° C. |
| *Bacillus cereus* | Laboratory strain (FIEROBE team LCB/CNRS) | TSB-24 H-37° C. |
| *Bacillus cereus* | CIP 66.24T | TSB-24 H-37° C. |
| *Bacillus cereus* paris | Laboratory strain (N. HENRY team/CNRS) | TSB-24 H-30° C. |
| *Bacillus subtilis* | Laboratory strain (GUISEPPI team LCB/CNRS) | LB-24 H-37° C. |
| *Cronobacter sakazakii* | CIP 103183T | TSB-24 H-37° C. |
| *Enterococcus durans* | Laboratory strain (FIEROBE team LCB/CNRS) | TSB-24 H-37° C. |
| *Enterococcus faecalis* | Laboratory strain (FIEROBE team LCB/CNRS) | TSB-24 H-37° C. |
| *Escherichia coli* K12 | MG1655 | LB-24 H-37° C. |
| *Escherichia coli* O86 | Laboratory strain (DENAMUR team/INSERM) | LB-24 H-37° C. |
| *Klebsiella pneumoniae* | CIP 101114 | TSB + 5% sheep blood-24 H-30° C. |
| *Klebsiella pneumoniae* | Clinical strain (LASCOLA/Marseille, LaTimone) | TSB-24 H-37° C. |
| *Kocuria varians* Paris | Laboratory strain (HENRY team/CNRS) | TSB-24 H-30° C. |
| *Lactococcus lactis lactis* | Laboratory strain (FIEROBE team LCB/CNRS) | TSB-24 H-30° C. |
| *Legionella pneumophila* sg1 Paris | CIP 33152 | YEC + sup. *Legionella* 10%-24 H-37° C. |
| *Legionella pneumophila* sg6 | LG 0846 3022 (CNRL, environmental strain) | YEC + sup. *Legionella* 10%-24 H-37° C. |
| *Listeria monocytogenes* 1/2 | CIP 82.110pT | BHI-24 H-37° C. |
| *Listeria monocytogenes* 1/2a | CIP 100607 | BHI-24 H-37° C. |
| *Micrococcus luteus* | Laboratory strain (FIEROBE team LCB/CNRS) | TSB-24 H-30° C. |
| *Neisseria gonorrhoeae* | CIP 79.18T | TSB + 10% Horse Blood-24 H-37° C. |
| *Neisseria meningitidis* | CIP 107858 | TSB + 10% Horse Blood-24 H-37° C. |
| *Proteus mirabilis* | Clinical strain (LASCOLA/Marseille, La Timone) | TSB-24 H-37° C. |
| *Providencia stuartii* | Clinical strain (LASCOLA/Marseille, La Timone) | TSB-24 H-37° C. |
| *Pseudomonas fluorescens* Migula | ATCC 4927 | TSB-24 H-37° C. |
| *Pseudomonas fluorescens* Paris | Laboratory strain (HENRY team/CNRS) | TSB-24 H-37° C. |
| *Rhodocycclus* | Laboratory strain (HENRY team/CNRS) | TSB-24 H-30° C. |
| *Salmonella typhimurium* 12023 | Laboratory strain (BARRAS team LCB/CNRS) | LB-24 H-37° C. |
| *Serratia marcescens* | CIP 102446 | TSB-24 H-30° C. |
| *Serratia marcescens* | Clinical strain (LASCOLA/Marseille, La Timone) | TSB-24 H-37° C. |
| *Shewanella oneidensis* | Laboratory strain (MEJEAN team LCB/CNRS) | LB-24 H-37° C. |
| *Staphylococcus aureus* | Clinical strain (DUKAN team LCB/CNRS) | TSB-24 H-37° C. |
| *Staphylococcus aureus aureus* | IP 53-156 | TSB-24 H-37° C. |
| *Staphylococcus epidermis* | Laboratory strain (FIEROBE team LCB/CNRS) | TSB-24 H-37° C. |
| *Staphylococcus saprophyticus* | Clinical strain (LASCOLA/Marseille, La Timone) | TSB-24 H-37° C. |
| *Stenotrophomonas maltophilia* | Clinical strain (LASCOLA/Marseille, La Timone) | TSB-24 H-37° C. |
| *Streptococcus agalactiae* | Clinical strain (LASCOLA/Marseille, La Timone) | TSB-24 H-37° C. |
| *Vibrio cholerae* | CIP 104151 | TSB-24 H-37° C. |
| EUKARYOTES | | |
| *Aspergillus niger* | Laboratory strain (FIEROBE team LCB/CNRS) | TSB-24 H-30° C. |
| *Candida albicans* | Laboratory strain (FIEROBE team LCB/CNRS) | TSB-24 H-30° C. |
| *Fusarium* | CNCM 1149-76 | TSB-24 H-30° C. |
| *Geotrichum candidum* | CNCM 1447-83 | TSB-24 H-30° C. |
| *Saccharomyces cerevisiae* | BY4741 | YPD + 10% glucose |
| *Acanthamoebae castellanii* | ATCC 30234 | PYG |

TABLE 2

| | Composition | Provider | Reference |
|---|---|---|---|
| Tryptic Soy Broth (TSB) | casein peptone (pancreatic) 17 g/l + Soya peptone (papain digest.) 3 g/l + Sodium chloride 5 g/l + Dipotassium hydrogen phosphate 2.5 g/l + Glucose 2.5 g/l pH 7.3 | Sigma Aldrich (USA) | 2209 |
| Brain Heart Infusion (BHI) | brain infusion solids 12.5 g/l + beef heart infusion solids 5 g/l + proteose peptone 10 g/l + glucose 2 g/l + sodium chloride 5 g/l + di sodium phosphate 2.5 g/l | Oxoid (GB) | CM113 |
| YEC | yeast extract 10 g/l + Casamino acid | Becton Dickinson (USA) | Bacto 212720 |
| PYG | Proteose peptone 20 g/L + yeast extract 1 g/L + glucose 18 g/L + calcium chloride + di sodium phosphate + potassium phosphate + magnesium sulphate + ° sodium citrate-PH = 6.5 | ATCC | 712 PYG |
| Luria Bertani (LB) | Bactotryptone 10 g/l+ | Becton Dickinson (USA) | 211699 |
| | Bacto yeast extract 5 g/l+ | Becton Dickinson (USA) | 212720 |
| | Sodium chloride+ | Sigma Aldrich (USA) | 55886 |
| | pastagar 15 g/l pH 7.2 | Biorad (USA) | 64946 |

1.2) Copper Catalyzed Click Chemistry

Overnight cultures were diluted 100 times in fresh medium (final volume 100 µl) containing Kdo-N$_3$(I-1) or Ara-N$_3$(Ia) (10 mM). Microorganisms were incubated at 30 or 37° C. for 24 hours and then washed 3 times with phosphate buffer (0.05 M, pH 7.5) by centrifugation at 13,000×g for 2 min at room temperature.

Two fluorochrome-alkyne probes of following formula A488-yne (6a) and A594-yne (6b) were used:

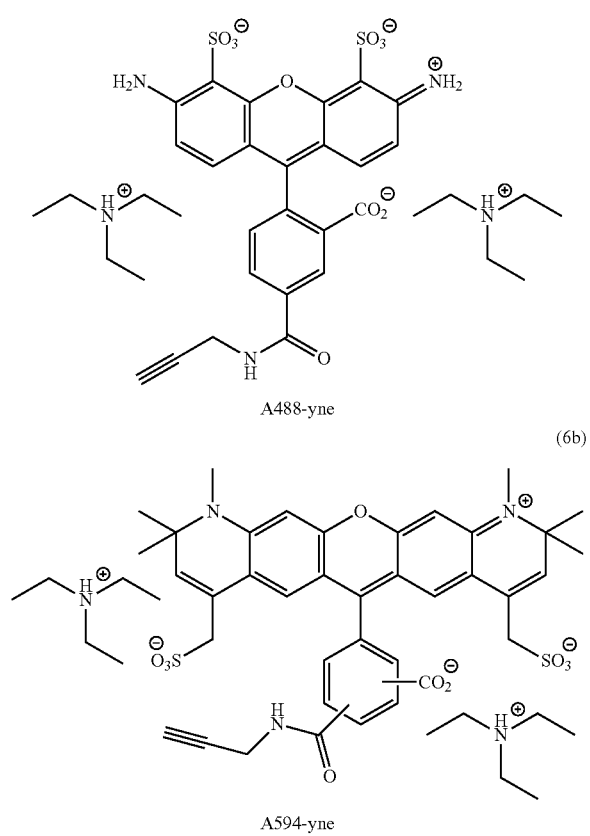

A488-yne (6a)

A594-yne (6b)

CuSO$_4$ and TGTA, at a final concentration of 2 mM and 4 mM respectively, were mixed overnight in phosphate buffer (0.05 M, pH 7.5) at 37° C. under vigorous shaking. Next, aminoguanidine, sodium ascorbate and A488-yne (6a) or A594-yne (6b) at a final concentration of 4 mM, 5 mM and 1 mM respectively were added to CuSO$_4$/TGTA overnight mix. Finally, microorganisms were re-suspended in this solution and incubated for 30 minutes at 37° C. under shaking. Finally, cells were then washed 3 times with phosphate buffer by centrifugation at 14,000×g for 2 min at room and analyzed by microscopy.

1.3) Fluorescence Microscopy.

Microorganisms were inoculated onto glass cover slips and covered with a thin (1 mm of thickness) semisolid 1% agar pad made with dilute LB (1/10 in phosphate buffer (0.05 M, pH 7.5)). Images were recorded with epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France).

2) Results

21.) Different Strains of Bacteria, Fungi and Amoebas have been Tested with Both Compounds Ara-N3 (Ia) of the Present Invention and Kdo-N$_3$ (I-1) of the Prior Art in Comparison.

These strains were grown first in the presence of compound (Ia) or (I-1) and the incorporation of the azido chemical reporter into the microorganism was monitored in a subsequent step, using copper-catalyzed azide-alkyne cycloaddition in the conditions previously described, with copper sulfate, sodium ascorbate, TGTA, a water-soluble tris (triazolyl) ligand for copper (I), and a fluorochrome-alkyne probe of above formula (6a) or (6b), for 30 minutes as above disclosed.

In these experiments, strains showing highly distinctive fluorescence, indicative of an effective metabolic incorporation of the chemical reporter have been marked "+" in the table 3 below and the absence of labeling has been marked "–" and the not tested bacteria have been marked "NT" in table 3.

TABLE 3

| Microorganisms | Kdo-N₃ | Ara-N₃ |
|---|---|---|
| BACTERIA | | |
| *Acinetobacter baumannii* | + | + |
| *Bacillus cereus* | NT | + |
| *Bacillus cereus* | NT | + |
| *Bacillus cereus* paris | NT | + |
| *Bacillus subtilis* | – | + |
| *Cronobacter sakazakii* | + | + |
| *Enterococcus durans* | NT | + |
| *Enterococcus faecalis* | – | + |
| *Escherichia coli* K12 | + | + |
| *Escherichia coli* O86 | + | + |
| *Klebsiella pneumoniae* | + | + |
| *Klebsiella pneumoniae* | + | + |
| *Legionella pneumophila* sg1 Paris | + | + |
| *Legionella pneumophila* sg6 | + | + |
| *Listeria monocytogenes* 1/2 | – | + |
| *Micrococcus luteus* | – | + |
| *Neisseria gonorrhoeae* | – | + |
| *Neisseria meningitides* | + | + |
| *Proteus mirabilis* | + | + |
| *Providencia stuartii* | + | + |
| *Pseudomonas fluorescens* Migula | + | + |
| *Pseudomonas fluorescens* Paris | + | + |
| *Salmonella typhimurium* 12023 | + | + |
| *Serratia marcescens* | + | + |
| *Serratia marcescens* | + | + |
| *Staphylococcus aureus* | – | + |
| *Staphylococcus aureus aureus* | – | + |
| *Staphylococcus epidermis* | – | + |
| *Staphylococcus saprophyticus* | NT | + |
| *Stenotrophomonas maltophilia* | + | + |
| *Streptococcus agalactiae* | NT | + |
| *Vibrio cholerae* | + | + |
| EUKARYOTES | | |
| *Aspergillus niger* | – | + |
| *Candida albicans* | – | + |
| *Fusarium* | – | + |
| *Geotrichum candidum* | – | + |
| *Acanthamoebae castellanii* | – | + |

These experiments show that compound (Ia) of the present invention is assimilated by a broad range of bacteria and Fungi as well as amoebas (all tested microorganisms were labeled). Interestingly, compound (Ia) is assimilated by the following bacteria (all Gram positive bacteria) and Fungi strains (all the tested Fungi) which did not assimilate compound (I-1):
  a) Bacteria: *Bacillus subtilis, Enterococcus faecalis, Neisseria gonorrhoeae, Listeria monocytogenes, Micrococcus luteus, Staphylococcus aureus, Staphylococcus aureus aureus*, and
  b) Fungi: *Aspergillus niger, Candida albicans, Fusarium* and *Geotrichum candidum*, and
  c) amoebas: *Acanthamoebae castellanii*.

The invention claimed is:
1. A method for labeling specifically living microorganisms in a sample comprising microorganisms, wherein said method comprises the steps of:
  a) incubating said microorganisms of said sample with at least one modified monosaccharide compound comprising a first reactive group Ra, which is capable to chemically react with a second reactive group, so that a residue bearing said first reactive group is incorporated into said living microorganisms, and
  b) contacting said residue incorporated into said microorganism with a labeling molecule comprising said second reactive group, for generating the chemical reaction of said first reactive group of said residue incorporated into said living microorganism with said second reactive group of said labeling molecule, resulting in a covalent link, wherein said modified monosaccharide compound has the following formula (I'), or a salt thereof:

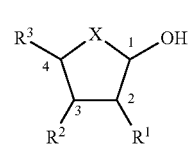

X is O, and

R1 and R2 are independently H, OH, or NH₂, wherein the OH and NH2 are each being substituted or not by a protecting group selected from the group consisting of alkyl, hydroxyalkyl, acyl, formyl and imidoyl groups, and R3 is an alkyl chain of $C_1$ to $C_4$, each carbon being substituted or not by OH or NH₂, wherein the OH or NH₂ being substituted or not by a protecting group selected from the group consisting of alkyl, hydroxyalkyl, acyl, formyl and imidoyl groups, R3 group being substituted by said first reactive group Ra, and wherein the first reactive group Ra is selected from the group consisting of an azido group, a group bearing an azido, an alkyne group, and a group bearing an alkyne, and said second reactive group is selected from the group consisting of an alkyne group, a group bearing an alkyne, an azido group, and a group bearing an azido, wherein said first reactive group is capable of reacting with said second reactive group via an azide alkyne cycloaddition.

2. The method according to claim 1, wherein said modified monosaccharide compound is a stereoisomer having the formula (I) or a salt thereof

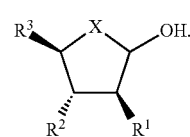

3. The method according to claim 1, wherein:
  R1 and R2 are OH, which is substituted or not by said protecting group, and
  R3 is —CH₃, —CH₂OH, or —CH₂NH₂, which is substituted by said first reactive group Ra.

4. The method according to claim 1, wherein said modified monosaccharide compound is a compound having the following stereoisomer formula (Ia), or a salt thereof:

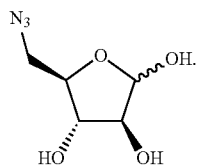

Ia

5. The method according to claim 1, wherein Ra is —N₃ or —C≡CH.

6. The method according to claim 1, wherein said microorganism is selected from the group consisting of:
Prokaryotic microorganisms, and
Unicellular eukaryotic microorganisms.

7. The method according to claim 6, for labeling one or more microorganisms selected from the group consisting of the following species microorganisms:
a) bacteria: *Acinetobacter baumannii, Bacillus cereus, Bacillus cereus, Bacillus cereus paris, Bacillus subtilis, Cronobacter sakazakii, Enterococcus durans, Enterococcus faecalis, Escherichia coli, Klebsiella pneumophila, Legionella pneumophila, Listeria monocytogenes, Micrococcus luteus, Neisseria gonorrhoeae, Neisseria meningitides, Proteus mirabilis, Providencia stuartii, Pseudomonas fluorescens Migula, Pseudomonas fluorescens Paris, Salmonella typhimurium, Serratia marcescens, Staphylococcus aureus, Staphylococcus aureus aureus, Staphylococcus epidermis, Staphylococcus saprophyticus, Stenotrophomonas maltophilia, Streptococcus agalactiae, Vibrio cholera*,
b) fungi: *Aspergillus niger, Candida albicans, Fusarium* and *Geotrichum candidum*, and
c) amoebas: *Acanthamoebae castellanii*.

8. The method according to claim 1, comprising the further step of:
c) detecting living microorganism in detecting whether said microorganism comprise said labeling molecule bound to said living microorganism and/or immobilizing said living microorganism bearing said labeling molecule onto a solid substrate, wherein said labeling molecule is a molecule comprising a detectable substance or capable to react or to be bound to a detectable substance or said labeling molecule is a first molecule bearing said second reactive group, said first molecule being capable to react or to be bound to a second molecule and/or to a solid substrate.

9. The method according to claim 8, wherein said labeling molecule is a detectable molecule comprising a detectable substance, wherein in step c), detecting living microorganism comprises detecting whether said microorganism comprise said detectable molecule bound to said microorganism.

10. The method according to claim 8, wherein said labeling molecule is a first ligand or first binding protein bearing said second reactive group and in step c) said living microorganism coupled to said first ligand or first binding protein is detected and/or immobilized by contacting said first ligand or first binding protein with a second ligand or second binding protein reacting or binding specifically to said first ligand or first binding protein.

11. A kit for carrying out the method of claim 1, which comprises:
said modified monosaccharide compound of formula (I),
said labeling molecule comprising said second reactive group capable of reacting with said first reactive group, and
optionally, reactants for generating the reaction of said first reactive group with said second reactive group of said labeling molecule.

12. The kit according to claim 11, which further comprises:
said detectable molecule or said second molecule bearing a detectable substance comprising a fluorochrome or luminescent molecule or an enzyme, and/or
a solid substrate bearing said second molecule capable of specifically reacting or binding with said labeling molecule.

13. The kit according to claim 12, which further comprises a culture or incubation medium allowing the growth of said microorganism.

\* \* \* \* \*

UNITED STATES PATENT AND TRADEMARK OFFICE
CERTIFICATE OF CORRECTION

Page 1 of 2

PATENT NO. : 11,187,705 B2
APPLICATION NO. : 15/570410
DATED : November 30, 2021
INVENTOR(S) : Sam Dukan It is certified that error appears in the above-identified patent and that said Letters Patent is hereby corrected as shown below:

In the Specification

• Column 4, Line 40, "ca" should read --can--

• Column 6, Line 55, "Fung" should read --Fungi--

• Column 7, Line 1, "*Neonickettsia*" should read --*Neorickettsia*--

• Column 7, Lines 3-4, "*Rhodocyccius*" should read --*Rhodocycclus*--

• Column 7, Line 6, "*Tenadbacu/um*" should read --*Tenacibaculum*--

• Column 7, Line 53, "cell/mi" should read --cell/ml--

• Column 9, Line 59, "Diels-Aider" should read --Diels-Alder--

• Column 12, Line 28, "F254" should read --F2s4--

• Column 13, Line 57, "Asa" should read --J4_sa--

• Column 13, Line 57, "H-Sa" should read --H-5al3--

• Column 13, Line 57, "H-Sba" should read --H-5ba--

• Column 13, Line 57, "H-Sb" should read --H-5bl3--

• Column 14, Line 46, "D20" should read --D2O--

• Column 15, in the References column of Table 1 at the bacteria *Listeria monocytogenes* 1/2, "CI P 82.11 0pT" should read --CI P 82.11 OT--

Signed and Sealed this
Twentieth Day of September, 2022

Katherine Kelly Vidal
*Director of the United States Patent and Trademark Office*

- Column 17, in the Reference column on Table 2, "2209" should read --22092--

- Column 17, in the Reference column on Table 2, "CM113" should read --CM1135--

- Column 19, Line 23 (in Table 3), "*Neisseria meningitides*" should read --*Neisseria meningitidis*--

- Column 19, Line 24 (in Table 3), "*Proteus mirabills*" should read --*Proteus mirabilis*--